US00PP11339P

United States Patent [19]

Fruehwirth

[11] Patent Number: Plant 11,339

[45] Date of Patent: Apr. 11, 2000

[54] POINSETTIA PLANT NAMED 'ECKADEL'

[75] Inventor: Franz Fruehwirth, Encinitas, Calif.

[73] Assignee: Paul Ecke Ranch, Inc., Encinitas, Calif.

[21] Appl. No.: 09/087,918

[22] Filed: Jun. 1, 1998

[51] Int. Cl.[7] ..... A01H 5/00

[52] U.S. Cl. ..... Plt./304

[58] Field of Search ..... Plt./304, 305

[56] References Cited

U.S. PATENT DOCUMENTS

P.P. 6,116 2/1988 Drewlow ..... Plt./304
P.P. 9,726 12/1996 Dummen ..... Plt./304

*Primary Examiner*—Howard J. Locker
*Assistant Examiner*—Kent L. Bell
*Attorney, Agent, or Firm*—C. A. Whealy

[57] ABSTRACT

A new and distinct variety of Poinsettia plant named 'Eckadel', characterized by its creamy white flower bracts that are deeply lobed; deeply lobed dark green leaves; upright plant habit; very freely branching habit; and excellent postproduction longevity.

1 Drawing Sheet

BACKGROUND OF THE INVENTION

The present invention relates to a new and distinct variety of Poinsettia plant, botanically known as *Euphorbia pulcherrima* Willd., and hereinafter referred to by the name 'Eckadel'.

The new vareity is a naturally-occurring branch mutation of the commercial *Euphorbia pulcherrima* Willd. cultivar '21-85', disclosed in U.S. Plant Pat. No. 7,250. The new Poinsettia was selected by the Inventor in a greenhouse in Encinitas, Calif., in 1996. The objective of the Inventor's Poinsettia development program is to create new Poinsettia cultivars having interesting bract and leaf display, desirable bract and foliage color and form, strong and freely branching stems and good post-production longevity.

Asexual reproduction of the new variety by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckadel'. These characteristics in combination distinguish 'Eckadel' as a new and distinct variety:

1. Creamy flower bracts that are deeply lobed.
2. Deeply lobed dark green leaves.
3. Upright plant habit.
4. Very freely branching habit.
5. Excellent postproduction longevity.

In side-by-side comparisons conducted by the Inventor in Encinitas, Calif., plants of the new Poinsettia differed from plants of '21-85' in the following characteristics:

1. Plants of the new Poinsettia are more compact, less vigorous and more upright than plants of '21-85'.

2. Leaves of plants of the new Poinsettia are more lobed than leaves of plants of '21-85'.

3. Flower bracts of plants of the new Poinsettia are more numerous, smaller and lobed compared to flower bracts of plants of '21-85'.

4. Plants of the new Poinsettia flower later than plants of the cultivar '21-85'.

BRIEF DESCRIPTION OF THE PHOTOGRAPH

The accompanying colored photograph illustrates the overall appearance of the new variety, showing the colors as true as it is reasonably possible to obtain in a colored reproduction of this type. The photograph comprises a side perspective view of a typical plant of 'Eckadel'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a polyethylene-covered greenhouse with day temperatues about 23° C., night temperatures about 17° C., and light levels about 40,000 lux. Plants were grown in 16.5-cm pots, pinched one time, and flowered under naturally lengthening nycotoperiods during the fall/early winter.

In the following description, color references are made to The Royal Horticultural Society Colour Chart except where general terms of ordinary dictionary significance are used.

Botanical classification: *Euphorbia pulcherrima* Willd. 'Eckadel'.

Parentage: Naturally-occurring branch mutation of *Euphorbia pulcherrima* Willd. cultivar '21-85', disclosed in U.S. Plant Pat. No. 7,250.

Propagation:

*Type cutting.*—Terminal cuttings.

*Time to initiate roots.*—Summer: About 12 to 18 days at 27° C. Winter: About 15 to 18 days at 24° C.

*Time to develop roots.*—Summer: About 26 days at 27° C. Winter: About 26 days at 24° C.

*Rooting habit.*—Thick, freely branching, becoming more fibrous with development.

Plant description:

*Plant form.*—Inverted triangle, top of plant rounded.

*Growth habit.*—Upright and somewhat spreading. Very freely branching. Branching is enhanced by removing the shoot apex. Moderately vigorous.

*Plant height.*—About 30 cm.

*Crop time.*—From unrooted cuttings to a flowering plant in a 16.5-cm container, about 20 weeks are required.

*Stem description.*—Number of lateral branches: About ten lateral branches are formed after removal of the terminal apex. Lateral branch length: About 21 cm. Internode length: About 7.5 mm. Stem color: 144B.

*Foliage description.*—Quantity of leaves per lateral branch: About 16. Length: About 10 cm. Width: About 7.5 cm. Shape: Ovate with deep lobes, oak-leaf shape. Apex: Acuminate. Base: Rounded to acute. Margin: Entire with three to five lobes, some deeply incised. Texture: Smooth, dull, mostly glabrous with very slight pubescence on lower surface. Aspect: Mostly flat. Color: Young foliage, upper surface: 137A. Young foliage, lower surface: 137C. Mature foliage, upper surface: 147A. Mature foliage, lower surface: 147B. Venation, upper surface: 147B. Venation, lower surface: 147C. Petiole: Length: About 4 cm. Diameter: About 2 mm. Color: 144B.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions.

*Quantity of inflorescences.*—One per lateral branch, usually about 10 per plant.

*Inflorescence size.*—Diameter: About 29 cm. Height (depth): About 3.5 cm.

*Flower bracts.*—Quantity of flower bracts per inflorescence: Usually about 12 primary bracts and about 15 secondary bracts per inflorescence. Length: About 11 cm. Width: About 11 cm. Shape: Ovate with deep lobes, oak-leaf shape. Apex: Abruptly acuminate. Base: Acute. Margin: Entire; Becoming deeply lobed with development, usually five lobed. Texture: Smooth, slightly glabrous. Aspect: Flat. Color: Developing, upper surface: 6D. Developing, lower surface: 6D. Mature, upper surface: 11C/11D. Mature, lower surface: 11C/11D.

*Cyathia.*—Quantity: Usually about 24 per corymb. Diameter of cyathia cluster: About 5.5 cm. Length: About 1.2 cm. Width: About 5 mm. Color: Immature: 144C. Mature: 144B. Peduncle: Length: About 3 mm. Aspect: Strong, erect. Color: 144C. Stamens: Stamen number: Numerous, typically about five per cyathium. Stamen color: 12D. Anther shape: Oval. Amount of pollen: Moderate. Pollen color: 12D. Pistils: Pistil number: 1 per cyathium. Stigma shape: Tri-lobate. Stigma color: 3C. Style length: About 2 mm. Style color: 144D. Nectary color: 14A.

Disease resistance: No fungal, bacterial nor viral problems observed on plants grown under commercial conditions.

Postproduction longevity: Generally plants maintain good substance and bract color for about four weeks under interior conditions.

It is claimed:

1. A new and distinct variety of Poinsettia plant named 'Eckadel', as illustrated and described.

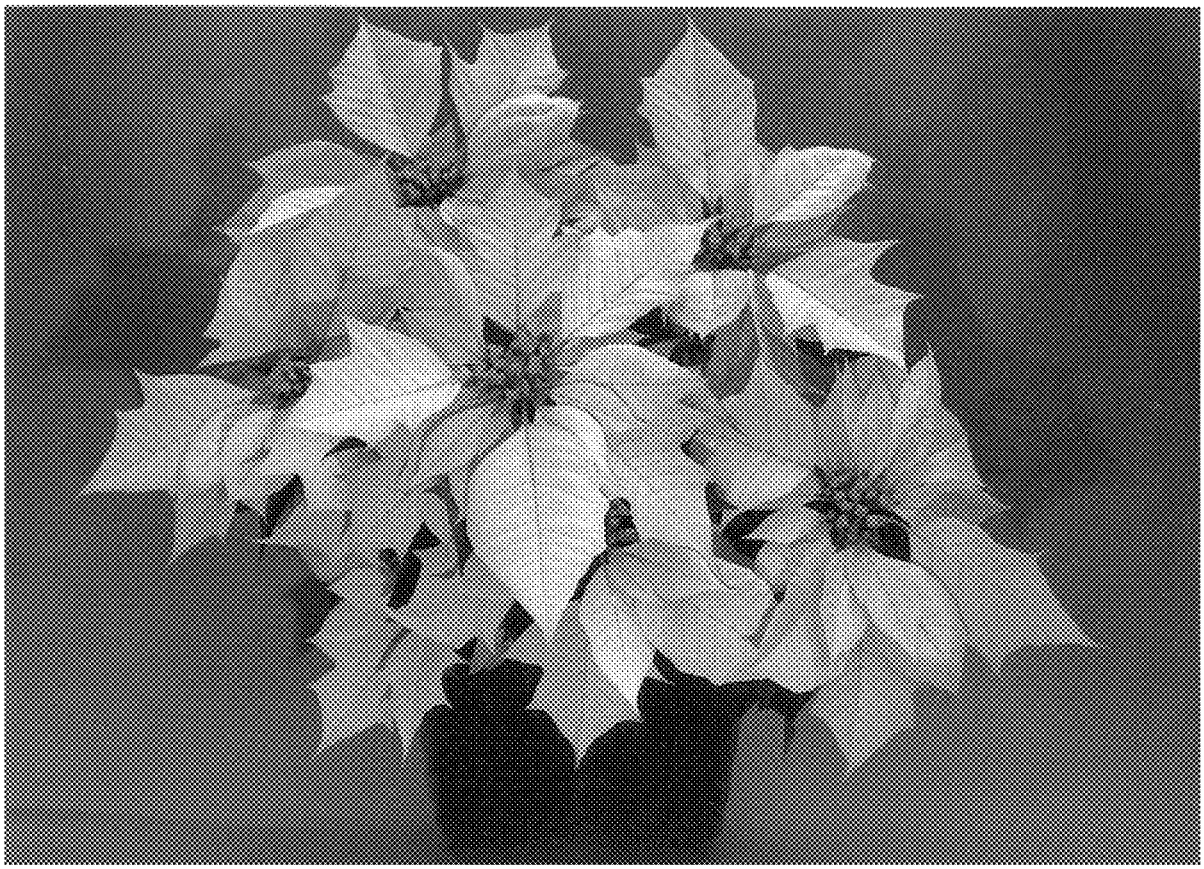

* * * * *